Figure 1:
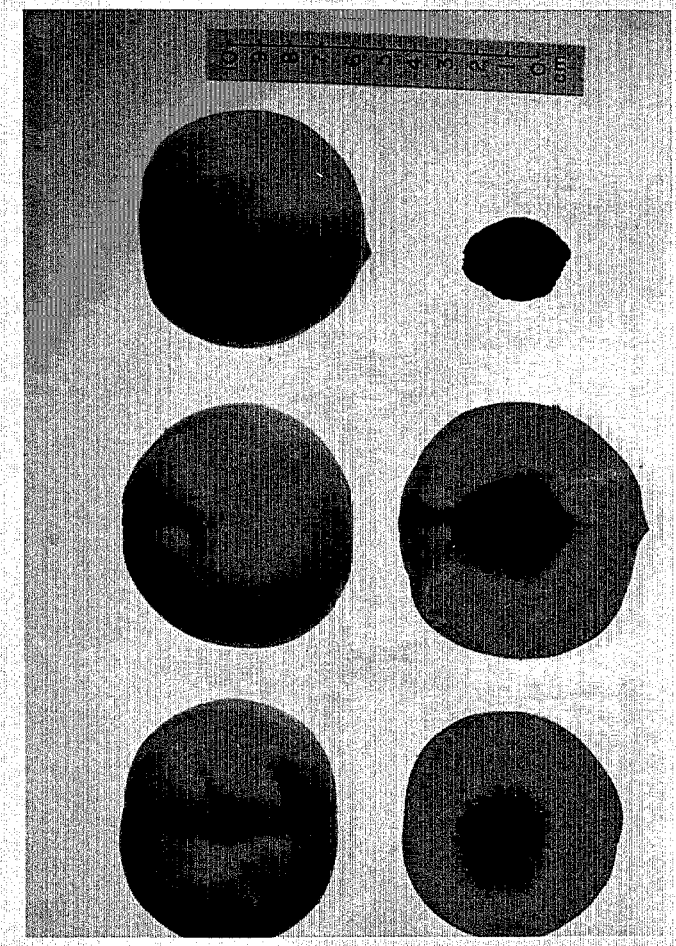

US00PP08332P

United States Patent [19]

Beutel et al.

[11] Patent Number: Plant 8,332

[45] Date of Patent: Aug. 3, 1993

[54] 'HESSE' CLINGSTONE PEACH TREE

[75] Inventors: James A. Beutel, Davis; James F. Doyle, Clovis; Robert E. Fenton, Big Bear Lake; James T. Yeager, Davis, all of Calif.

[73] Assignee: The Regents of the University of California, Berkeley, Calif.

[21] Appl. No.: 809,895

[22] Filed: Dec. 18, 1991

[51] Int. Cl.[5] ..... A01H 5/00

[52] U.S. Cl. ..... Plt./43.1

[58] Field of Search ..... Plt./43.1

*Primary Examiner*—James R. Feyrer

*Attorney, Agent, or Firm*—Townsend and Townsend Khourie and Crew

[57] ABSTRACT

The 'Hesse' variety of peach tree is a high quality canning clingstone peach in the extra late maturity group. The peach is productive and ripens from late in August to early September and addresses the need for a high quality canning clingstone peach to replace the extra late but poor quality cultivar 'Corona'.

1 Drawing Sheet

DESCRIPTION

This invention relates to a new variety of clingstone peach tree and more particularly to one which is extra late in maturity.

Selection 18, 6-60 of this variety, named 'Hesse', resulted from an open-pollinated seed of University of California clingstone peach selection H6-55 'Riegles'. Seed of 'Riegles' was collected by Robert Fenton in 1973. This seed was planted in the Davis nursery of the University of California Department of Pomology in 1974 and the resultant seedling trees were planted in January of 1975 in a seedling block (Block 18) located at the Wolfskill Experimental Orchard, Winters, Calif.

In the Drawings:

FIG. 1 shows fruit which is typical of the new variety with views of the stem cavity, apex and suture, skin and flesh color and the stone.

The seedling of 'Hesse' first bore fruit in 1977 and it was selected that same year. Canned samples of the fruit of 'Hesse' were shown to the industry at the Cannera League of California annual Fruit Sample Cutting at San Francisco in January of 1978. Subsequently, 'Hesse' was asexually reproduced by the grafting of scions of the variety onto rootstock located at the 20 Block at the Wolfskill Experimental Orchard and the "R" Block at the Davis Nursery in 1979. Fruit of 'Hesse' has been canned for evaluation and evaluated by both University of California and Cling Peach Industry personnel for over 10 years. Below is a table summarizing data for a number of advanced cling peach selections, including 'Hesse', for the years 1980 through 1985.

As shown by the table, productivity is reflected by the column headed "Crop Load Rating". 'Hesse' scored an average of 2.5 on a scale of 2 (moderate) and 3(heavy). The score was derived over a six year period which reflects positively on the regularity of bearing.

Average Data for Samples Processed 1980–1985

| | Selection | Appearance | Flavor | Case Yield |
|---|---|---|---|---|
| Extra | 19, 4–40 | 3.2 | 7.4 | 59.1 |
| Earlies | D6-15W | 3.0 | 7.2 | 58.5 |
| | 19, 3–17 | 3.2 | 7.3 | 59.6 |
| Earlies | Andross | 2.8 | 7.0 | 58.9 |
| | 7, 8–103 | 3.1 | 7.0 | 61.1 |

-continued

Average Data for Samples Processed 1980–1985

| | | | | |
|---|---|---|---|---|
| | N23-9W | 3.1 | 7.0 | 60.0 |
| Lates | Ross | 2.9 | 6.4 | 59.4 |
| | Dr. Davis | 3.1 | 7.0 | 60.2 |
| | 19, 2–72 | 3.3 | 6.7 | 60.0 |
| Extra | 18, 4–45 | 3.2 | 7.0 | 60.2 |
| Lates | 'Hesse' | 3.2 | 7.6 | 60.1 |
| | 18, 8–23 | 3.2 | 6.6 | 60.5 |

| | Crop Load Rating | Harvest Firmness | Harvest Diameter |
|---|---|---|---|
| Extra | 2.8 | 8.0 | 61.5 |
| Earlies | 3.0 | 7.3 | 62.4 |
| | 2.5 | 6.1 | 60.5 |
| Earlies | 2.8 | 7.3 | 63.2 |
| | 1.5 | 9.8 | 72.7 |
| | 2.5 | 9.2 | 64.5 |
| Lates | 3.0 | 9.1 | 71.4 |
| | 3.0 | 9.1 | 66.6 |
| | 2.5 | 10.2 | 60.1 |
| Extra | 2.8 | 8.6 | 68.3 |
| Lates | 2.5 | 8.4 | 63.8 |
| | 3.0 | 10.0 | 67.7 |

Appearance: 1 = poor, 2 = acceptable, 3 = good or choice, 4 = excellent.
Flavor: 5 = poor, 6 = acceptable, 8 = high flavor, 10 = very high flavor.
Case Yield: Number of cases per ton of peaches.
Crop Load Rating: 1 = light, 2 = moderate, 3 = heavy.
Harvest Firmness: Pounds pressure of flesh at harvest.
Harvest Diameter: Average size in mm. 60 mm = 2⅜ inches diameter.

The above table indicates that 'Hesse', when compared with 'Ross' and 'Dr. Davis', is either the same or slightly better in appearance, and has a definitely better flavor. It also has about the same case yield, a poorer crop load rating, and a poorer harvest firmness. The harvest diameter is smaller but the maturity of 'Hesse' is later.

SPECIFIC DESCRIPTION

The description which follows was made from fruit and plant material of 'Hesse' obtained in the second week of September 1990. The fruit is described as full, firm-ripe maturity. Color definitions used in the description are from "Dictionary of Color" by Maerz and Paul, published in 1950.

Tree description:

*Form.*—Above average in size and vigor. Tree upright to upright-spreading in form, with eventual form and density determined by pruning. Productive and hardy under typical California interior valley climatic conditions. The width of the crown of the trees ranged from 8 feet 8 inches to 10 feet 4 inches after the fourth growing season. During the third growing season the trees attained a height of 12 feet and during the next growing season developed from 5 feet 6 inches to 6 feet 8 inches with new extension growth in the tops of the trees. Thus, the height of the trees at the end of the fourth growing season was some 17 feet 6 inches to 18 feet 8 inches overall. Internode length of fruiting hanger wood in a relatively horizontal positional ranges from 22 to 28 mm.

*Branches, trunk and bark.*—Shoots from current season's growth in a light green (18-J-5). Shoot surfaces exposed to direct sunlight often tinged with red. The trunk of the tree is average in caliper. Trunk bark texture is moderately rough with average amounts of scarfskin present. Bark color is medium brownish grey (8-H-9 Rembrandt Brown). Numerous large lenticels are present. Lenticel openings are often surrounded by slightly raised light brown callous tissue (7-E-11 Trotteur Tan). Branch lenticels are also present, usually small in size and of variable color. The color ranges from a light tan on the youngest shoots (11-F-4) to a medium brown on more mature shoots (15-C-11 Malay Brown).

*Leaves.*—Leaf measurements have been taken from leaves growing on vigorous upright current season's shoots. Leaves are large in size, average length is 17.8 cm including the petiole. Average leaf width is 3.3 cm.

*Leaf form.*—Linear lanceolate. Leaf tip acuminate. Tip usually is twisted sideways.

*leaf color.*—Upper leaf surface color is a dark green (22-H-9). Color of underside of leaf a lighter green (21-J-8). Midvein on underside of leaf is a pale green (20-I-4).

*Leaf margin.*—Margin form crenate. Crenations are well defined and regular. Crenations are tipped with a dark brown trichome. Leaf margins are slightly undulate.

*leaf petiole.*—Petiole length is moderately long, averaging 14.0 mm. Petiole thickness average 1.8 mm. Petiole color is a light green (20-H-8).

*Leaf glands.*—Glands are predominantly globose. Two to three glands are located on the leaf petiole. These glands are usually stalked. An additional one to two glands are preesnt on the basal leaf margin and these glands are not as strongly stalked as those on the petiole. Gland position is alternate. Gland color is a light, shiny green (19-K-6), but gland color darkens substantially with age.

*Leaf stipules.*—Long, averaging 17.0 mm. Stipules are very early deciduous.

Fruit description:

*Maturity.*—This new clingstone cultivar is in the extra late maturity group. It ripens late in August to early September in the same season as the current commercial cultivar 'Corona'.

*Fruit size.*—Uniform and large. Average check diameter is 76.3 mm, average suture diameter is 73.8 mm, average axial diameter is 83.3 mm.

*Fruit form.*—Uniform, nearly symmetrical. Globose in lateral aspect. Apical aspect is nearly globose.

*Fruit suture.*—Distinct line from base to apex. Suture is slightly depressed near the apex. No distinct suture color is apparent. Very slight stitching is present along the suture line.

*Ventral surface.*—Smooth, rounded, almost no lipping.

*Stem cavity.*—Broad, moderately deep and oval in form. Average length is from 40 to 43 mm, average width is 31 to 35 mm. Cavity is moderately deep 20 to 22 mm.

*Fruit base.*—Rounded. Base angle variable from right angle to oblique.

*Fruit apex.*—Generally rounded with a low tip. Pistil point usually apical. Slight depression is present on ventral suture next to the apex.

*Stem.*—Moderately long, averaging 14 mm for the stem plus the basal attachment to the branch. Average stem thickness is 5.0 mm. Stem color is a light green (18-K-4).

*Skin.*—Pubescent, but with a very fine short matted pubescence. No observed tendency to crack.

*Skin color.*—Primary ground color is a uniform yellow-orange (10-J-5). Only a small amount of blush color is present on exposed fruit, from 0 to 25 percent of the entire fruit surface. The blush pattern is usually striped or dappled. Blush color is a dull red, from a lighter red (6-L-7) to deeper red tones (7-L-8).

*Flesh color.*—A uniform yellow from skin to stone cavity (10K-4). Color is slightly darker in stone cavity (10-K-6).

*Flesh texture.*—Fine, non-melting.

*Flesh fibers.*—Medium length, fine in texture, few in number.

*Ripening.*—Ripens uniformly.

*Flavor.*—Fruit develops excellent quality, rich in flavor and well balanced. Flavor scores, as shown on the table of page 3, reflect a 7.6 average throughout the test period, higher than other widely planted clingstone cultivars such as Andross' (7.0), 'Ross' (6.4) and 'Dr. Davis' (7.0).

*Aroma.*—Slight to lacking.

Stone description:

*Attachment.*—Full clingstone.

*Stone size.*—Medium to slightly below average. Average length is 33.3 mm, average width is 23.8 mm, average thickness is 18.5 mm.

*Fibers.*—Numerous short fibers attached laterally to the stone surface.

*Form.*—Variable, from obovate to almost oval.

*Base.*—Moderately narrow and medium truncate in form. Base angle is variable but most often slightly oblique to the stone axis, shorter on the ventral suture side.

*Hilum.*—Medium to small in size and well defined. Hilum is surrounded by a raised and heavily grooved collar.

*Apex.*—Acute in form with a sharp acuminate tip.

*Stone sides.*—Variable, from equal to slight unequal in size.

*Stone surface.*—Coarse and substantially grooved, especially basally and over the apical shoulders.

*Ventral edge.*—Moderately broad with several low wings converging apically. Wings are most prominent from mid-suture to the stone base.

*Dorsal edge.*—Broad and moderately coarse with a deep groove from slightly above mid-suture downwards (basally) to (but not through) the hilium collar. The upper (apical shoulder) area of the dorsal suture is substantially eroded and often concave in shape.

*Stone color.*—Dry color a light Khaki brown (13-B-5).

*Tendency to split.*—No tendency observed.

Floral description:

The floral description for 'Hesse' is of the flowers obtained from trees growing at the Wolfskill Experimental Orchard near Winters, Calif. The flowers reached full bloom stage on Feb. 24, 1991. The number of chilling hours at Winters were at 1100 hours below 45° F. for the 1990–91 season. This number of hours represents a slightly lower than normal chilling hour accumulation for the winter season.

*Bloom timing.*—Average in time of bloom in relation to other commercial cling peach cultivars. Date of full bloom at Winters, Calif. was Feb. 24, 1991.

*Flower size.*—Medium in size. This cultivar has a bloom that is non-showy in form but is the highest size range of this form. Average flower diameter is 24 mm when the flower is fully open.

*Bloom quantity.*—Abundant, most commonly two flowers per node.

*Flower buds and scales.*—Bud scale color is a medium brown (Trotteur Tan 7-E-11). Buds medium in size and conic in form. Bud scales are highly pubescent.

*Flower petals.*—Broadly oval to slightly ovate in form. Average petal length is 14 mm, average petal width is 11.5 mm. Petal color is a light pink in the center of the petal (2-E-1) with a slightly darker pink coloration on the outer petal margins (1-H-1). The petal claw is short, moderately broad and truncate. Claw color is a dark pink (1-E-3). Petal margins are moderately undulate, more so at the petal apices. The entire petal is generally cupped inwards. The apex of the petal is usually rounded with no tip. The number of petals present on any one flower is five.

*Flower pedicel.*—Very short in length, from 0.5 to 1.0 mm. Average thickness is 1.0 mm. Color of the pedicel is a bright shiny green (17-K-7). Pedicel surface is glabrous.

*Nectaries.*—Color of nectaries is a bright orange (11-J-11).

*Anthers.*—The anthers are average in size. Anther coloration is a tan ventrally (11-G-4) and a dull red-orange dorsally (Lacquer Red 4-K-11).

*Pollen.*—Abundant in quantity. Pollen coloration is a bright yellow (9-L-2). The tree of this variety is self-fertile and thus pollinates itself.

*Stamens.*—Moderately long and about equal to the exertion of the pistil when the flower is fully mature. Filament color is nearly opened, darkening to a light purple with senscence (Old Rose 4-I-2).

*Pistil.*—Pistil length average is 16 mm including the ovary. Pistil color is a very light green (17-G-3). Pistil surface is highly pubescent.

Fruit shipping and storage: The fruit goes directly to the cannery from the field and, therefore, the shipping characteristics of the fruit of this variety were not assessed. The fruit has a storage capacity of from 4 to 5 weeks in the cannery.

Fruit use: A non-melting clingstone peach in the extra late maturity group with potential for utilization in the canning and fruit processing industries. This cultivar addresses the need for a high quality canning cling to replace the existing poor quality cultivar 'Corona'.

We claim:

1. The new and distinct variety of clingstone peach tree illustrated and described herein and having the characteristics above enumerated.

* * * * *